US009671393B2

(12) United States Patent
Palhan et al.

(10) Patent No.: US 9,671,393 B2
(45) Date of Patent: Jun. 6, 2017

(54) CELLS FOR CHROMATIN IMMUNOPRECIPITATION AND METHODS FOR MAKING

(75) Inventors: Vikas B. Palhan, St. Louis, MO (US); Carol Kreader, St. Louis, MO (US); Ernie Mueller, St. Louis, MO (US)

(73) Assignee: SIGMA-ALDRICH CO., LLC, St. Louis, MO (US)

( * ) Notice: Subject to any disclaimer, the term of this patent is extended or adjusted under 35 U.S.C. 154(b) by 0 days.

(21) Appl. No.: 13/821,181

(22) PCT Filed: Sep. 2, 2011

(86) PCT No.: PCT/US2011/050326
§ 371 (c)(1),
(2), (4) Date: Mar. 25, 2013

(87) PCT Pub. No.: WO2012/033714
PCT Pub. Date: Mar. 15, 2012

(65) Prior Publication Data
US 2013/0172198 A1 Jul. 4, 2013

Related U.S. Application Data

(60) Provisional application No. 61/380,570, filed on Sep. 7, 2010.

(51) Int. Cl.
*G01N 33/53* (2006.01)
*G01N 1/44* (2006.01)
*C12N 1/20* (2006.01)
*G01N 33/68* (2006.01)

(52) U.S. Cl.
CPC ........... *G01N 33/5308* (2013.01); *C12N 1/20* (2013.01); *G01N 1/44* (2013.01); *G01N 33/6803* (2013.01); *G01N 33/6875* (2013.01)

(58) Field of Classification Search
CPC .......................... G01N 33/5308; G01N 1/44
USPC ......................................................... 506/1, 2
See application file for complete search history.

(56) References Cited

U.S. PATENT DOCUMENTS

| | | | |
|---|---|---|---|
| 4,124,598 A * | 11/1978 | Hearst et al. | 549/282 |
| 4,727,027 A | 2/1988 | Wiesehahn et al. | |
| 4,868,311 A * | 9/1989 | Saffran et al. | 548/304.1 |
| 5,221,608 A | 6/1993 | Cimino et al. | |
| 5,399,719 A | 3/1995 | Wollowitz et al. | |
| 6,448,047 B2 * | 9/2002 | Dattagupta et al. | 435/91.1 |
| 2004/0197343 A1 * | 10/2004 | Dubensky et al. | 424/184.1 |
| 2005/0037349 A1 * | 2/2005 | Picard et al. | 435/6 |
| 2009/0215029 A1 * | 8/2009 | Lawler | C12N 15/1006 435/5 |

FOREIGN PATENT DOCUMENTS

EP 2614137 A2 7/2013
WO WO 2008088839 A2 * 7/2008

OTHER PUBLICATIONS

Crotty et al., Tracking Human Antigen-Specific Memory B Cells: A Sensitive and Generalized ELISPOT System, J. Immunological Methods, 2004, 286, 111-122.*
Witt, H., Chromatin Immunoprecipitation (CHIP) Assay Protocol, 2007, 1-12.*
UNH Microarray Centre, Chromatin Immunoprecipitation Protocol, Staph A Cell Method, 2008, 1-11.*
Darling et al., Low-Speed Centrifugation Of Retroviral Vectors Absorbed To A Particulate Substrate: A Highly Effective Means of Enhancing Retroviral Titre, Gene Therapy, 2000, 7, 914-923.*
Dahl et al., A Rapid Micro Chromatin Immunoprecipitation, Nature Protocols Assay (uChIP), Nature Protocols, 2008, 3(6), 1032-1045.*
Noll et al., Formation and Repair of Interstrand Cross-Links in DNA, Chem. Rev., 2006, 106(2), 277-301.*
Invitrogen, Protein A-Sepharose 4B Conjugate, 2008, 1-2.*
Badshah et al., The Leader Polypeptide Of Theiler's Murine Encephalomyelitis Virus Is Required For The Assembly Of Virons il Mouse L Cells, Journal of Virology, 2000, 74(2), 875-882.*
Song et al., Review Article, Photochemistry and Photobiology of Psoralens, Photochemistry and Photobiology, 1979, 29, 1177-1197.*
World Health Organizatin (WHO), Laboratory Biosafety Manual, 3rd edition, 2004, 1-186.*
Maillard et al., Efficacy and Mycobactericidal Action of Aldehydes: Structure-Activity Relationship, New Biocides in Development, Chapter 8, American Chemical Society, 2007, 162-181.*
Smith et al., Rapid Characterization of Cross-Links, Mono-adducts, and Non-covalent binding of psoralens to deoxyoligonucleotides by LC-UV/ESI-MS and IRMPD Mass Spectrometry, 2010, Analyst, 2010, 135(5), 943-952.*
Eisenbrand, G., Toxicological Assessment of Furocoumarins in Foodstuffs, DFG—Senate Commission on Food Safety, 2006, 1-30.*
Cimino et al., Psoralens As Photoactive Probes of Nucleic Acid Structure and Function: Organic chemicstry, Photochemistry, and Biochemistry, Ann. Rev. Biochem., 1985, 54, 1151-1193.*
Minami et al., New Approach to Use Ethidium Bromide Monoazide as an Analytical Tool, Journal of Applied Microbiology, 2010, 109, 900-909.*
Brecher, M. et al., "Evaluation of bacterial inactivation in prestorage pooled, leukoreduced, whole blood-derived platelet concentrates suspended in plasma prepared with photochemical treatment," Transfusion, Oct. 2007, pp. 1896-1901, vol. 47.
Hurt, D. et al., "Antibody-nucleic acid interactions. Antibodies to psoralen-modified RNA as probes of RNA structure," Nucleic Acids Research, 1987, pp. 9057-9073, vol. 15, No. 21.
Nocker, A. et al., "Selective Removal of DNA from Dead Cells of Mixed Bacterial Communities by Use of Ethidium Monoazide," Applied and Environmental Microbiology, Mar. 2006, pp. 1997-2004, vol. 72, No. 3.

(Continued)

Primary Examiner — Amy M Bunker
(74) Attorney, Agent, or Firm — Polsinelli PC

(57) ABSTRACT

The present invention provides isolated, non-viable bacterial cells comprising a plurality of nucleic acid crosslinks, methods for making said cells, and methods for using said cells to isolate DNA-protein complexes. In particular, the nucleic acids of the cells are crosslinked by contacting the cells with a furocoumarin compound and ultraviolet light.

5 Claims, 2 Drawing Sheets

(56) References Cited

OTHER PUBLICATIONS

Oginsky, E. et al., "Lethal Photosensitization of Bacteria With 8-Methoxypsoralen to Long Wave Length Ultraviolet Radiation," J. Bacteriology, May 28, 1959, pp. 821-833, vol. 78.

International Search Report and Written Opinion dated Apr. 9, 2012 for related International Patent Application No. PCT/US2011/50326; 10 pages.

Supplementary European Search Report from related European Application No. EP 11 82 3989, dated Jun. 5, 2015; 6 pgs.

Brockstedt et al., "Killed but metabolically active microbes: a new vaccine paradigm for eliciting effector T-cell responses and protective immunity", Nature Medicine, 2005, pp. 853-860, vol. 11, No. 8.

Pelletier et al., "Pathogen inactivation techniques", Best Practice & Research Clinical Haematology, 2006, pp. 205-242, vol. 19, No. 1.

Rueckert et al., "Removal of contaminating DNA from polymerase chain reaction using ethidium monoazide", Journal of Microbiological Methods, 2007, pp. 596-600, vol. 68.

Weinmann et al., "Identification of unknown target genes of human transcription factors using chromatin immunoprecipitation", Methods, 2002, pp. 37-47, vol. 26.

* cited by examiner

CELLS FOR CHROMATIN IMMUNOPRECIPITATION AND METHODS FOR MAKING

FIELD OF THE INVENTION

The present invention generally relates to bacterial cells comprising a plurality of nucleic acid crosslinks, methods for making said cells, and methods for using said cells to isolate DNA-protein complexes.

BACKGROUND OF THE INVENTION

Chromatin immunoprecipitation (ChIP) is a research tool that is used to identify DNA binding sites in the genome for a particular protein of interest. For this, DNA-binding proteins in living cells are reversibly crosslinked to the DNA to which they are bound. The chromatin-protein complexes are then captured using an antibody against the protein of interest. The chromatin-protein-antibody complexes generally are isolated by contact with an immobilized protein that binds antibodies. For example, protein A of *Staphylococcus* binds the Fc domain of antibodies. Thus, isolated protein A may be immobilized on a solid support and used to capture chromatin-protein-antibody complexes. Alternatively, heat-inactivated *Staphylococcus* cells in which protein A and other cell wall proteins have been fixed in place (i.e., Staph A cells) may be used to isolate the chromatin-protein-antibody complexes. Not only are Staph A cells much cheaper, but also they are better suited for isolating DNA bound by low abundance proteins due to their high protein A content.

One problem of using Staph A cells, however, is that the DNA-protein complexes isolated with Staph A cells may be contaminated with *Staphylococcus* DNA. In PCR or hybridization based applications (e.g., ChIP-on-chip) using sequence-specific primers or probes, the contaminating *Staphylococcus* DNA does not interfere with analysis of the isolated DNA of interest. In DNA sequencing applications (e.g., ChIP-Seq) or other sequence-independent methods, however, the contaminating *Staphylococcus* DNA does interfere with the analysis. Although DNA blocking procedures such as incubating Staph A cells with agents such as herring sperm DNA and bovine serum albumin have been developed, there still exists a need for more effective procedures for inactivating the chromosomal DNA of *Staphylococcus* cells such that it does not interfere with sequence-independent procedures (i.e., those requiring strand separation).

SUMMARY OF THE INVENTION

Among the various aspects of the present disclosure is the provision of an isolated, non-viable bacterial cell comprising a plurality of nucleic acid crosslinks.

Another aspect of the disclosure encompasses a method for preparing a cell comprising a plurality of nucleic acid crosslinks. The method comprises contacting an isolated, non-viable bacterial cell with a furocoumarin compound to form a furocoumarin-containing cell. The method further comprises contacting the furocoumarin-containing cell with a source of ultraviolet light to form the cell comprising the plurality of nucleic acid crosslinks.

A further aspect of the present disclosure provides a kit for chromatin immunoprecipitation. The kit comprises a plurality of non-viable bacterial cells comprising a plurality of cell wall protein crosslinks and a plurality of nucleic acid crosslinks, the cells being able to bind DNA-protein-antibody complexes such that DNA-protein complexes are isolated.

Yet another aspect of the disclosure encompasses a method for isolating a plurality of DNA-protein complexes. The method comprises contacting a plurality of DNA-protein-antibody complexes with a plurality of non-viable bacterial cells comprising a plurality of cell wall protein crosslinks and a plurality of nucleic acid crosslinks such that the bacterial cells bind the DNA-protein-antibody complexes to form a plurality of bacterial cell-bound DNA-protein-antibody complexes. The method further comprises contacting the bacterial cell-bound DNA-protein-antibody complexes with an elution buffer to form the plurality of isolated DNA-protein complexes, wherein the DNA-protein complexes are substantially devoid of bacterial cell-derived nucleic acids that are detectable by a technique requiring strand separation.

Other features and iterations of the disclosure are described in more detail below.

DETAILED DESCRIPTION OF THE INVENTION

Figure 1:
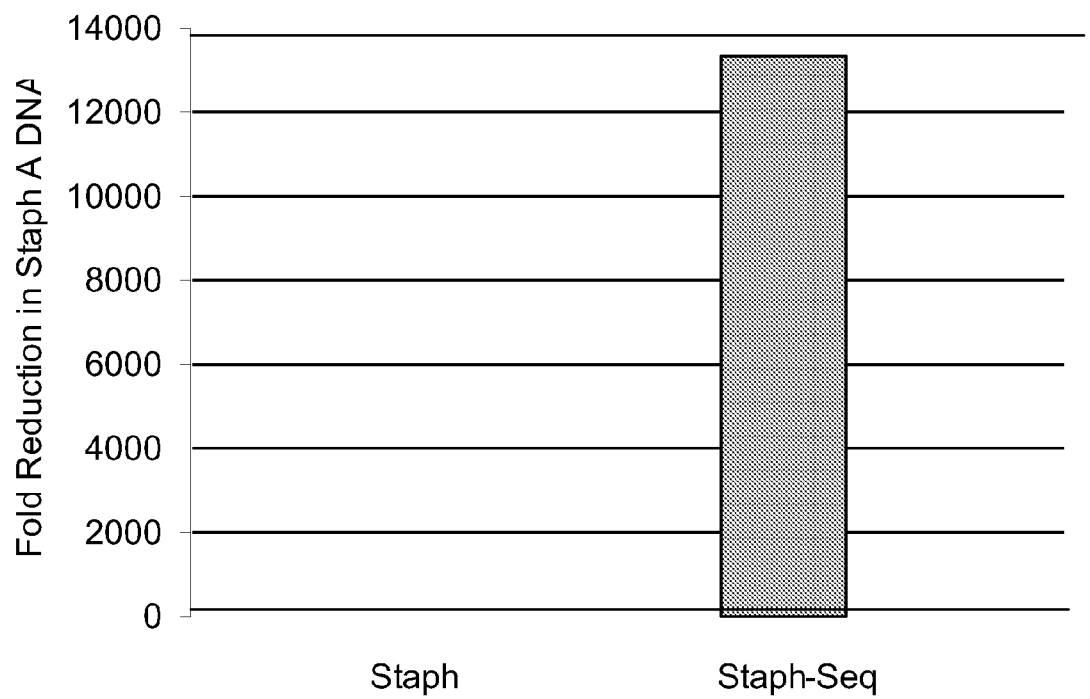
FIG. 1 illustrates the reduction of contaminating *Staphylococcus* DNA in cells treated with aminomethyl trioxsalen (AMT). Plotted is the fold reduction in *Staphylococcus* DNA in qPCR reactions using primers specific for *Staphylococcus* RNA coding sequences in ChIP eluates prepared using Staph A cells (untreated) and Staph-Seq cells (AMT-treated).

The present disclosure provides isolated, non-viable bacterial cells comprising a plurality of nucleic acid crosslinks, and kits comprising the isolated, non-viable bacterial cells comprising the nucleic acid crosslinks, wherein the crosslinked nucleic acids are unable to undergo strand separation and, consequently, are unable to participate in strand separation-based enzymatic nucleic acid amplification or detection procedures. Also provided are methods for making the bacterial cells comprising the nucleic acid crosslinks. Briefly, the method comprises contacting bacterial cells with an ultraviolet light-activatable crosslinking agent, wherein the nucleic acids of the cell are crosslinked such that they are unable to undergo strand separation. The disclosure also provides methods for using the bacterial cells comprising the nucleic acid crosslinks to isolate DNA-protein complexes, wherein the isolated DNA-protein complexes are substantially devoid of bacterial cell-derived nucleic acids that are detectable by a procedure that requires strand separation.

(I) Isolated, Non-Viable Bacterial Cell Comprising Nucleic Acid Crosslinks

One aspect of the disclosure encompasses an isolated, non-viable bacterial cell comprising a plurality of nucleic acid crosslinks. The isolated, non-viable bacterial cell may further comprise a plurality of cell wall protein crosslinks.

(a) Bacterial Cells

The bacterial cell may be a Gram-positive bacterial cell, a Gram-negative bacterial cell, or a Gram-indeterminate bacterial cell. Suitable genera of Gram-positive bacteria include *Staphylococcus, Streptococcus, Peptostreptococcus, Corynebacterium, Clostridium, Listeria*, and *Bacillus*. Gram-negative genera may include Enterobacteriaceae, *Pseudomonas, Moraxella, Helicobacter, Stenotrophomonas, Bdellovibrio*, and *Legionella*. In preferred embodiments, the bacterial cell may be a *Staphylococcus, Streptococcus*, or *Peptostreptococcus* cell. In other preferred embodiments, the bacterial cell may be a protein A-positive *Staphylococcus* cell, a protein G-positive *Streptococcus* cell, or a protein L-positive *Peptostreptococcus* cell. In an exemplary embodiment, the bacterial cell may be a *Staphylococcus aureus* Cowan strain 1 cell.

The bacterial cell may further comprise cell wall proteins that are crosslinked. In some embodiments, the cell wall proteins may be crosslinked by a small molecule crosslinker. Suitable small molecule crosslinkers include imidoester crosslinkers (e.g., dimethyl adipimidate, dimethyl pimelimidate, dimethyl suberimidate, dimethyl 3,3'-dithiobispropionimidate, and the like), NHS-ester crosslinkers (e.g., bis(sulfosuccinimidyl) suberate, disuccinimidyl glutarate, dithiobis(succinimidyl) propionate; disuccinimidyl suberate, disuccinimidyl tartrate, and so forth), or an aldehyde fixative (e.g., formaldehyde, paraformaldehyde, glutaraldehyde, and the like). In other embodiments, the cell wall proteins may be crosslinked by photoreactive amino acid analogs, such as diazirine analogs. In one embodiment, the cell wall proteins may be crosslinked or fixed by contact with an aldehyde fixative. A preferred aldehyde fixative is formaldehyde.

Typically, the isolated bacterial cell is non-viable. For example, the bacterial cell may be killed by treatment with heat. Those of skill in the art are familiar with a variety of heat treatments that made be used to inactivate or kill the bacterial cell. As an example, the bacterial cell may be heated to a temperature of about 75-80° C. for about five minutes.

(b) Nucleic Acid Crosslinks

The isolated, non-viable bacterial also comprises crosslinked nucleic acids. The nucleic acid that is crosslinked may be DNA, RNA, or combinations thereof. The DNA may be chromosomal or extrachromosomal. The RNA may be messenger RNA (mRNA), microRNA (miRNA), non-coding RNA (ncRNA), or another small RNA. The nucleic acid may be double-stranded, such as, e.g., a DNA-DNA hybrid, DNA-RNA hybrid, mRNA/miRNA hybrid, and so forth. The nucleic acid may be single-stranded and may comprise a secondary structure (i.e., hairpins, stems, loops, and the like). In general, the nucleic acid crosslinks are interstrand crosslinks such that the two strands may not be separated or denatured. Stated another way, the crosslinked nucleic acid does not undergo strand separation. In a preferred embodiment, the crosslinked nucleic acid may comprise chromosomal DNA interstrand crosslinks.

In general, each nucleic acid crosslink comprises a covalently bound furocoumarin molecule. Furocoumarins are compounds that are activated by ultraviolet light to form covalent adducts with pryrimidines. The covalent adduct may be a monoadduct (i.e., an intramolecular adduct) or a diadduct (i.e., an intermolecular adduct). Thus, the nucleic acid crosslinks in the cell are formed by contact with a furocoumarin and ultraviolet light.

(c) Furocoumarins

In one embodiment, the furocoumarin may be a compound comprising Formula (I) or an isomer thereof:
wherein:

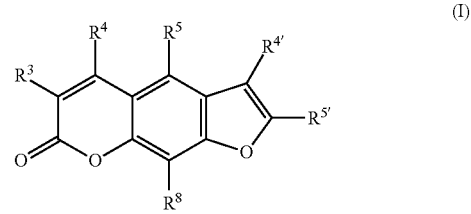

$R^3, R^4, R^5, R^{4'}, R^{5'}$, and $R^8$ are independently chosen from hydrogen, amino, halogen, hydroxy, hydrocarbyl, and substituted hydrocarbyl.

In various embodiments, $R^3, R^4, R^5, R^{4'}, R^{5'}$, and $R^8$ may be independently chosen from hydrogen, amino, halogen, hydroxy, alkyl, substituted alkyl, alkoxy, substituted alkyoxy, alkoxyalkyl, substituted alkoxyalkyl, aminoalkyl, substituted aminoalkyl, haloalkyl, substituted haloalkyl, hydroxyalkyl, substituted hydroxyalkyl, alkenyl, substituted alkenyl, aryl, and substituted aryl.

In one iteration, each of $R^3, R^4, R^5, R^{4'}, R^{5'}$, and $R^8$ may be hydrogen, such that furocoumarin compound may be psoralen or its isomer, angelicin. In another iteration, each of $R^3, R^4, R^5, R^{4'}$, and $R^{5'}$ may be hydrogen and $R^8$ may be methyoxy, such that the furocoumarin compound may be 8-methoxy psoralen. In a further iteration, each of $R^3, R^5$ and $R^{4'}$ may be hydrogen, and each of $R^4, R^{5'}$, and $R^8$ may be methyl, such that the furocoumarin compound may be 4,5',8-trimethyl psoralen or trioxsalen. In still another iteration, each of $R^3$ and $R^5$ may be hydrogen, each of $R^4, R^{5'}$, and $R^8$ may be methyl, and $R^{4'}$ may be alkyl, substituted alkyl, alkoxy, substituted alkyoxy, alkoxyalkyl, substituted alkoxyalkyl, aminoalkyl, substituted aminoalkyl, haloalkyl, substituted haloalkyl, hydroxyalkyl, or substituted hydroxyalkyl. In yet another iteration, each of $R^3$ and $R^5$ may be hydrogen, each of $R^4, R^{5'}$, and $R^8$ may be methyl, and $R^{4'}$ may be aminomethyl, such that the furocoumarin compound may be 4'-aminomethyl trioxsalen.

(II) Methods for Preparing Cells Comprising Nucleic Acid Crosslinks

Another aspect of the disclosure encompasses methods for preparing the cells of the invention, which are detailed above in section (I). In general, the method comprises contacting an isolated, non-viable bacterial cell with (a) a furocoumarin compound and (b) a source of ultraviolet (UV) light.

(a) Contact with a Furocoumarin Compound

The first step of the method comprises contacting isolated bacterial cells with a furocoumarin compound to form furocoumarin-containing cells. Suitable bacterial cells are detailed above in section (I)(a). The bacterial cells may be live or non-live (i.e., dead) at the time of contact with the furocoumarin compound. Typically, the bacterial cells further comprise crosslinked cell wall proteins, as detailed above in section (I)(a). In preferred embodiments, the cells may be protein A-positive *Staphylococcus*, protein G-positive *Streptococcus*, or protein L-positive *Peptostreptococcus* cells. In an exemplary embodiment, the bacterial cells may be *Staphylococcus aureus* Cowan strain 1 cells. Furthermore, the *Staphylococcus aureus* Cowan strain 1 cells may be formaldehyde-fixed, heat-treated.

Typically, live bacterial cells are suspended in a suitable culture medium and non-live bacterial cells are resuspended in a suitable reaction buffer. Non-limiting examples of suitable reaction buffers include Tris, phosphate, and phosphate-buffered saline buffers. The buffer may further comprise a chelator, such as EDTA. The density of bacterial cells in the buffer or culture medium can and will vary. Typically, the cell density may range from about 0.01 g/mL to about 0.05 g/mL, from about 0.05 g/mL to about 0.25 g/mL, or from about 0.25 g/mL to about 1 g/mL. In preferred embodiments, the cell density may range from about 0.1 g/mL to about 0.3 g/mL. In an exemplary embodiment, the cell density may be about 0.2 g/mL.

Suitable furocoumarin compounds are detailed above in section (I)(c). The amount of furocoumarin compound that is contacted with the bacterial cells can and will vary. In general, the final concentration of the furocoumarin compound may range from about 0.01 mg/mL to about 2 mg/mL. In various embodiments, the final concentration of the furocoumarin may range from about 0.01 mg/mL to about 0.05 mg/mL, from about 0.05 mg/mL to about 0.25 mg/mL, from about 0.25 mg/mL to about 1 mg/mL, or from about 1 mg/mL to about 2 mg/mL. In preferred embodiments, the final concentration of the furocoumarin may range from about 0.1 mg/mL to about 0.7 mg/mL. In an exemplary embodiment, the final concentration of the furocoumarin may be about 0.5 mg/mL.

The period of time the bacterial cells are contacted with the furocoumarin compound to form the furocoumarin-containing cells may vary. Typically, the duration of contact between the bacterial cell and the furocoumarin compound may range from about 1 minute to 2 hours. However, contact with the furocoumarin compound may proceed for more than 2 hours without affecting the scope of the invention. In certain embodiments, the duration of contact may range from about 1 minute to about 10 minutes, from about 10 minutes to about 30 minutes, or from about 30 minutes to about 2 hours. In preferred embodiments, the duration of contact between the bacterial cell and the furocoumarin compound may range from about 5 minutes to about 30 minutes. In an exemplary embodiment, the duration of contact may be about 15 minutes.

Contact with the furocoumarin compound may occur at a temperature from about 0° C. to about 40° C. In various embodiments, the temperature may range from about 0° C. to about 10° C., from about 10° C. to about 20° C., from about 20° C. to about 30° C., or from 30° C. to about 40° C. In preferred embodiments, the temperature may range from about 20° C. to about 37° C. In an exemplary embodiment, contact with the furocoumarin compound may occur at about room temperature (i.e., about 23° C. to about 25° C.).

Contact between the bacterial cells and the furocoumarin compound typically occurs with agitation. The agitation may be orbital rotation, rocking rotation, shaking rotation, rolling rotation, end-for-end rotation, vortexing, and other means that are well known in the art. Additionally, contact between the bacterial cell and the furocoumarin compound may occur in the dark (i.e., in the absence of daylight).

(b) Contact with UV Light

The method further comprises contacting the furocoumarin-containing cells with a source of UV light, such that the furocoumarin compound is activated and nucleic acid crosslinks are formed in the cells. Types of nucleic acid crosslinks are described above in section (I)(b).

The wavelength of the UV light that is used in the method of the invention may vary. In general, the wavelength of the UV light may range from about 200 nm to about 400 nm. In one embodiment, the UV light may be middle UV light (MUV) and range from about 200 nm to about 300 nm. In another embodiment, the UV light may be near UV light (NUV) and range from about 300 nm to about 400 nm. In preferred embodiments, the UV light may be long wave ultraviolet A (UVA) and range from about 315 nm to about 400 nm. In various embodiments, the wavelength of the UV light may be about 300 nm, about 302 nm, about 312 nm, or about 365 nm. In an exemplary embodiment, the wavelength of the UV light may be about 365 nm.

The dose of UV light that is contacted with the bacterial cells can and will vary. In general, the dose of UV light may range from about 1 $J/cm^2$ to about 10 $J/cm^2$. In certain embodiments, the dose of UV light that is contacted with the bacterial cells may range from about 1-2 $J/cm^2$, 2-3 $J/cm^2$, 3-4 $J/cm^2$, 4-5 $J/cm^2$, 5-6 $J/cm^2$, 6-7 $J/cm^2$, 7-8 $J/cm^2$, 8-9 $J/cm^2$, or 9-10 $J/cm^2$. In preferred embodiments, the dose of UV light may range from about 2 $J/cm^2$ to about 6 $J/cm^2$. In an exemplary embodiment, the dose of UV light that is contacted with the bacterial cells may be about 4.6 $J/cm^2$.

The intensity of the UV light may also vary. Generally, the intensity of the UV light may range from about 0.5 $mW/cm^2$ to about 5 $mW/cm^2$. In some embodiments, the UV light intensity may range from about 0.5 $mW/cm^2$ to about 1 $mW/cm^2$, from about 1 $mW/cm^2$ to about 2 $mW/cm^2$, or from about 2 $mW/cm^2$ to about 5 $mW/cm^2$. Preferably, the UV light intensity may range from about 1 $mW/cm^2$ to about 3 $mW/cm^2$. In an exemplary embodiment, the UV light intensity may be about 1.7 $mW/cm^2$.

The UV light may be from a variety of sources. Non-limiting sources of UV light include UV transilluminators, UV crosslinker apparatus, UV lamps, UV laser diodes, UV solid state lasers, UV LEDs, and so forth. In an exemplary embodiment, the source of UV light may be a UV transilluminator.

The period of time the furocoumarin-containing cells are contacted with the UV light may vary. In general, the duration of contact with UV light may range from about 5 minutes to about 3 hours. In certain embodiments, the furocoumarin-containing cell may be contacted with UV light for about 5 minutes, about 10 minutes, about 20 minutes, about 30 minutes, about 40 minutes, about 50 minutes, about 60 minutes, about 90 minutes, about 120 minutes, or about 180 minutes. In preferred embodiments, the duration of contact may range from about 30 minutes to about 60 minutes. In an exemplary embodiment, the furocoumarin-containing cells may be contacted with UV light for 45 minutes.

Contact between the furocoumarin-containing cells and the UV light may occur at a temperature from about 0° C. to about 30° C. In various embodiments, the temperature may range from about 0° C. to about 10° C., from about 10° C. to about 20° C., or from about 20° C. to about 30° C. In a preferred embodiment, contact with the UV light may occur at a temperature that ranges from about 2° C. to about 10° C. In an exemplary embodiment, contact with the UV light may occur at about 4° C.

Typically, the furocoumarin-containing cells are dispersed as a thin layer in a suitable container such that exposure to the UV light is optimized. The amount of cell suspension per exposure area can and will vary. Generally, the amount of cell suspension per unit area may range from about 0.01 $ml/cm^2$ to about 0.5 $ml/cm^2$. In various embodiments, the amount of cell suspension per unit area may range from about 0.01 $ml/cm^2$ to about 0.05 $ml/cm^2$, from about 0.05 $ml/cm^2$ to about 0.2 $ml/cm^2$, or from about 0.2 $ml/cm^2$ to about 0.5 $ml/cm^2$. In preferred embodiments, the amount of cell suspension per unit area may range from about 0.05 ml/cm² to about 0.2 ml/cm². In an exemplary embodiment, the amount of cell suspension per unit area may be about 0.1 ml/cm².

Additionally, the cells may be agitated during contact with the UV light. The agitation may be orbital rotation, rocking rotation, shaking rotation, or another suitable motion.

(c) Pretreatment of Cells Prior to Contact with the Furocoumarin Compound

Prior to contact with the furocoumarin compound (see section (II)(a), above), the bacterial cells may be contacted with a surfactant and a reducing agent.

Non-limiting examples of suitable surfactants include alkyl sulfates (such as sodium dodecyl sulfate, ammonium lauryl sulfate, and the like); alkyl ether sulfates (such as sodium laureth sulfate, sodium myreth sulfate, and so forth); alkyl sulfonates; alkyl aryl sulfonates; alkyl aryl ether phosphates; silyl ether phosphates; silyl carboxylates; and carboxylate fluorosurfactants. In an exemplary embodiment, the surfactant may be sodium dodecyl sulfate.

The concentration of the surfactant can and will vary. Typically, the concentration of the surfactant may range from about 1% to about 10%. In various embodiment, the concentration of the surfactant may be about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%. In an exemplary embodiment, the concentration of the surfactant may be about 3%.

Suitable reducing agents include, without limit, beta-mercaptoethanol and dithiothreitol. In an exemplary embodiment, the reducing agent may be beta-mercaptoethanol.

The concentration of the reducing agent may vary. In general, the concentration of the reducing agent may range from about 1% to about 30%. In certain embodiment, the concentration of the surfactant may be about 1%, 2%, 3%, 4%, 5%, 6%, 7%, 8%, 9%, 10%, 11%, 12%, 13%, 14%, 15%, 16%, 18%, 20%, 22%, 24%, 26%, 28%, or 30%. In an exemplary embodiment, the concentration of the reducing agent may be about 10%.

Contact with the surfactant and the reducing agent may be conducted at a temperature that ranges from about 80° C. to about 120° C. In some embodiments, the temperature of the contacting step may be about 80° C., 85° C., 90° C., 95° C., 100° C., 105° C., 110° C., 115° C., or 120° C. In an exemplary embodiment, contact with the surfactant and the reducing agent may be conducted at about 100° C.

The period of time the cells are contacted with the surfactant and the reducing agent can and will vary. Generally, the duration of time may range from about 5 minutes to about 3 hours. In certain embodiments, contact with the surfactant and the reducing agent may proceed for about 5 minutes, about 10 minutes, about 20 minutes, about 30 minutes, about 40 minutes, about 50 minutes, about 60 minutes, about 90 minutes, about 120 minutes, or about 180 minutes. In preferred embodiments, the duration of contact may range from about 15 minutes to about 60 minutes. In an exemplary embodiment, contact with the surfactant and the reducing agent may proceed for about 30 minutes.

(d) Posttreatment

After contact with the UV light (as detailed in section (II)(b) above), the cells comprising the nucleic acid crosslinks may be washed with a suitable buffer (see buffers listed in section (II)(a) above). That is, the cells may be sedimented by centrifugation, the supernate solution removed, the cells resuspended in suitable wash buffer, and the cycle repeated several times. The final resuspension of cells may be aliquoted into smaller volumes and used fresh or snap-frozen in liquid nitrogen before long-term storage at −70° C. The cells may be lyophilized for long term storage at room temperature. A suitable lyophilization protocol is detailed in the Examples. Those of skill in the art appreciate that other lyophilization procedures may be used.

(III) Kit for Chromatin Immunoprecipitation

Another aspect of the disclosure provides chromatin immunoprecipitation kits comprising the cells of the invention, which are non-viable bacterial cells comprising a plurality of nucleic acid crosslinks and a plurality of cell wall protein crosslinks. Thus, the cells are able to bind the antibodies of DNA-protein-antibody complexes and isolate DNA-protein complexes from cellular mixtures. Advantageously, because the cells of the invention comprise nucleic acid crosslinks, nucleic acids derived from the cells of the invention are unable to undergo strand separation, and consequently, are unable to participate in strand-separation based enzymatic nucleic acid amplification reactions, such as, e.g., PCR reactions and DNA sequencing reactions. Accordingly, nucleic acids derived from the bacterial cells of the invention that are associated with the isolated DNA-protein complexes will not interfere with analysis of the DNA in the isolated DNA-protein complexes.

The kit of the invention, therefore, comprises at least one container holding an aliquot of the bacterial cells of the invention. The kit may include one or more additional reagents useful for chromatin immunoprecipitation procedures. Suitable reagents may include, without limit, cell resuspension buffers, dilution buffers, binding buffers, wash buffers, elution buffers, salt solutions, and protease inhibitors. Suitable buffers are well known in the art. The kit generally also includes instructions to practice chromatin immunoprecipitation using the cells of the invention.

(IV) Methods for Isolating DNA-Protein Complexes

An additional aspect of the disclosure encompasses methods for isolating DNA-protein complexes using the bacterial cells of the invention, wherein the isolated DNA-protein complexes are substantially devoid of bacterial cell-derived nucleic acids that are detectable by a procedure requiring strand separation. The method comprises contacting a plurality of DNA-protein-antibody complexes with the cells of the invention, wherein the cells bind the antibodies of the DNA-protein-antibody complexes to form a plurality of bacterial cell-bound DNA-protein-antibody complexes. The method further comprises contacting the bacterial cell-bound DNA-protein-antibody complexes with an elution buffer to form the plurality of isolated DNA-protein complexes that are substantially devoid of bacterial cell-derived nucleic acids that are detectable by a technique requiring strand separation. Plainly stated, substantially all of the bacterial cell-derived nucleic acids associated with the isolated DNA-protein complexes are unable to undergo strand separation because of the nucleic acid crosslinks, and consequently, cannot be detected by a procedure that requires strand separation.

Those of skill in the art are familiar with techniques for forming the DNA-protein-antibody complexes. Contact between the bacterial cells of the invention and the DNA-protein-antibody complexes to form the bacterial cell-bound DNA-protein-antibody complexes typically is performed in the presence of a binding buffer. Suitable binding buffers are well known in the art. The method may further comprise a series of wash steps, during which unbound materials are removed from the bacterial cells. Suitable wash buffers and wash protocols are well known in the art. The final step of the method comprises contacting the bacterial cell-bound DNA-protein-antibody complexes with an elution buffer to form the isolated DNA-protein complexes. Again, examples of suitable elution buffers are well known in the art.

Typically, the isolated DNA-protein complexes are heat-treated to reverse the DNA-protein crosslinks such that the DNA is isolated and may be analyzed. A variety of techniques are suitable for analyzing the isolated DNA. In preferred embodiments, the isolated DNA may be analyzed by massively parallel DNA sequencing techniques using a genome sequencer. Non-limiting examples of suitable sequencing techniques include sequencing-by-synthesis techniques (e.g., Solexa sequencing; Illumina, Inc); sequencing-by-ligation (e.g., SOLiD™, Sequencing by Oligonucleotide Ligation and Detection; Applied Biosystems, Inc.); 454 pryosequencing; Ion Torrent proton detection sequencing, paired-end tag (PET) sequencing, cluster amplification methods, and bridge amplification methods. The isolated DNA may also be analyzed by PCR based methods, hybridization based methods, or microarray based methods. As detailed above, substantially all of the bacterial cell-derived nucleic acids associated with the isolated DNA-protein complexes comprise nucleic acid interstrand crosslinks and will not interfere with analysis of the DNA isolated from the DNA-protein complexes.

DEFINITIONS

To facilitate understanding of the invention, the following terms are defined.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

As used herein, the term "crosslink" refers to a bond that links one biological polymer with another biological polymer. The biological polymers may be nucleic acids, proteins, or combinations thereof. The bond may be covalent or non-covalent. Accordingly, both covalent and non-covalent crosslinks may be reversible.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Aminomethyltrioxsalen Treatment of Staphylococcus areus Cells

The following example details crosslinking of the chromosomal DNA of heat-treated, formaldehyde-fixed, protein A-containing Staphylococcus areus (Staph A) cells by contact with 4'-aminomethyl trioxsalen (AMT) and UVA light. The starting material was two bottles of 10 g of Staph A cells. Each white Staph A pellet (settled at the bottom of the supplied bottle) was resuspended in 50 mL of dialysis buffer (2 mM EDTA, 50 mM Trizma-HCl, pH 8) by pipetting repeatedly with a 25 ml pipette. Each Staph A suspension was transferred to a 50 ml plastic conical centrifugation tube and centrifuged at 5645×g for 5 minutes at 4° C. (e.g., with a JA25.5 fixed angle rotor in a Beckman J2-HS centrifuge at 6000 rpm).

The supernatants were removed and each cell pellet was resuspended in 20 ml of dialysis buffer using a glass rod and by pipetting repeatedly with a 25 ml pipette. Then the volume in each tube was brought to 40 ml with dialysis buffer, and the cells were centrifuged at 5645×g for 5 minutes at 4° C. (as above).

The supernatants were removed and each Staph A pellet was resuspended in 15 ml (×2) of boiling buffer (1×PBS, 3% SDS, and 10% β-mercaptoethanol in a fume hood. The pellets were resuspended using a glass rod followed by repeated pipetting. Each Staph A cell suspension was transferred into a fresh 50 ml conical tube.

The two conical tubes (with slightly loose caps) were immersed in a boiling water bath for 30 minutes. The boiling water bath was set up in a 500 ml glass beaker with 300 ml of deionized water, 10-15 glass beads and a magnetic stirrer on a heated stir. During the 30 min boiling step, each tube of cells was manually swirled five times every 10 minutes. The tubes remained immersed in boiling water during the boiling step.

After 30 minutes, the tubes were removed from the boiling water and allowed to cool. Each suspension was transferred to a fresh 50 ml conical tube and centrifuged at 5645×g (see above) for 5 minutes at room temperature (~25° C.).

Each supernatant was removed (into chemical waste receptacle in a fume hood) and each cell pellet was washed with 40 ml of dialysis buffer. First, each pellet was resuspended in 20 ml of dialysis buffer using a glass rod and repeated pipetting with a 25 ml pipette until the clumps were no longer visible, and the volume in each tube was made up to 40 ml with dialysis buffer. The tubes were centrifuged at 5645×g for 5 minutes at room temperature. The supernatants were discarded. Each cell pellet was washed with another 40 ml of dialysis buffer as detailed above.

Each boiled Staph A pellet was resuspended in 20 ml of dialysis buffer containing 0.5 gm/ml 4'-aminomethyl trioxsalen (AMT) using a clean glass rod. Each suspension was pipetted repeatedly using a 10 ml pipette until no cell clumps were visible. The two resuspensions were pooled into one tube, which was tightly capped and covered with aluminum foil. The tube was rotated end-to-end for 15 minutes at room temperature to form AMT-bound Staph A cells.

The AMT-bound Staph A cell suspension (approximately 50 ml) was transferred onto a prechilled 245 mm×245 mm Nunc dish sitting on ice in a tray. The tray containing the dish of cells was placed on a Lo profile rocker inside the UVA cross-linker (UltraLum CEX-1500; UltraLum Inc., Claremont, Calif.). The dish of cells was rocked at the slowest speed possible and care was taken to ensure that the cell suspension mixed end-to-end without spilling over the edge of the dish. The lid of the dish was removed and the cells were exposed to UVA light (365 nm, 4.6 J/cm$^2$, and 1.7 mW/cm$^2$) for 45 minutes while rocking continuously.

The cell suspension was transferred to 50 ml conical tubes, centrifuged as above, and washed two times with 40 ml of dialysis buffer. Each cell pellet was resuspended in 40 ml of dialysis buffer as detailed above. Care was taken to ensure that the cells were resuspended uniformly without any visible cell clumps. Aliquots (0.2 ml) of the cells were transferred to 1.8 ml screw cap cryovials (the lids were kept slightly loose to allow gas exchange during lyophilization) and the cells were snap frozen by immersion in liquid nitrogen. The vials were placed in a lysophilizer set at −35° C. and the tubes were allowed to equilibrate at −35° C. for 15 minutes. The temperature was raised from −35° C. to 0° C. over 90 minutes. The temperature was held at 0° C. for 12 hours. The temperature was raised to 25° C. over 15 minutes and held for 1 hour. The tubes were removed, tightly capped, and stored at room temperature. The AMT-treated Staph A cells are called "Staph-Seq" cells.

Example 2

Reduction of Amplifiable Staphylococcus DNA in ChIP Eluates

The Staph-Seq cells prepared in Example 1 were used to isolate DNA-protein complexes using standard procedures (i.e., ChIP). Untreated (control) Staph A cells were also used to isolate DNA-protein complexes. The amount of amplifiable contaminating *Staphylococcus* DNA in each preparation was estimated by qPCR using primers specific for *Staphylococcus* RNA coding sequences. The results are presented below in TABLE 1.

TABLE 1

Contaminating DNA in ChIP complexes prepared with untreated and AMT-treated cells

| Sample | Ct | ΔCt | Fold Reduction |
| --- | --- | --- | --- |
| Staph A (control) | 21.3 | 0 | 1 |
| Staph-Seq (AMT-treated) | 35 | −13.7 | 13,308 |

The amount of contaminating *Staphylococcus* DNA was reduced by more than 13.000-fold (also see FIG. 1), indicating that amplifiable chromosomal *Staphylococcus* DNA in the AMT-treated cells was substantially reduced.

Example 3

Improved ChIP-Seq Using Staph-Seq Cells for ChIP

Figure 2:
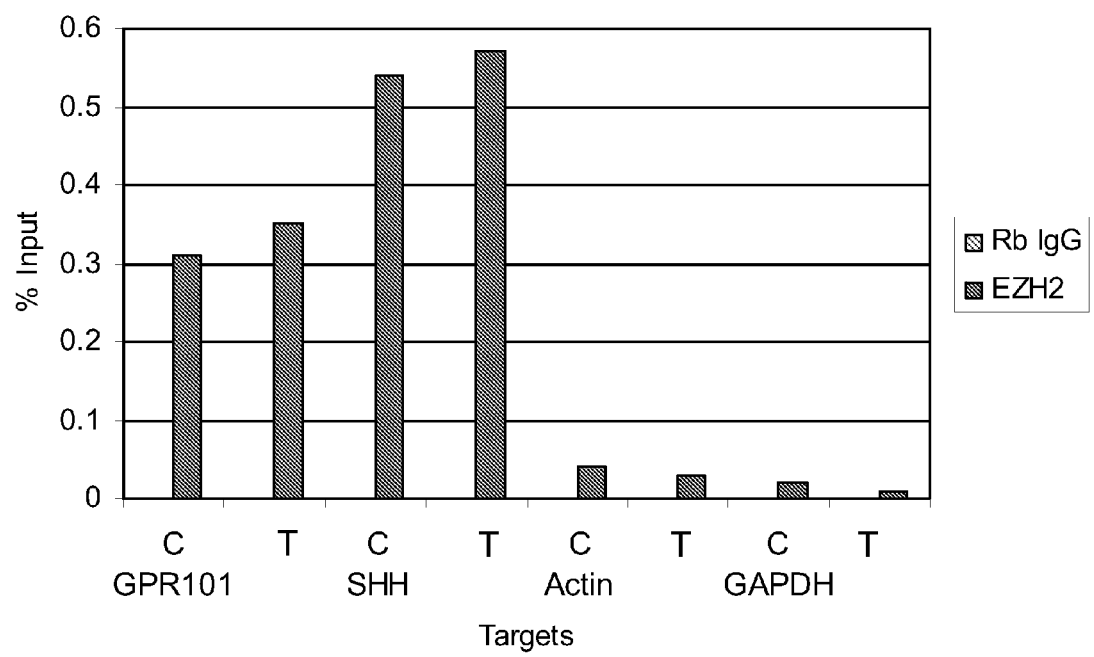
FIG. 2 shows the recruitment of the DNA-binding protein EZH2 on target genes, GPR101 and SHH. Non-target genes are actin and GAPDH. Plotted is the % input for qPCR using complexes immunoprecipitated with antibodies against EZH2 or control rabbit IgGs (i.e., there was no input). C: control, untreated Staph A cells. T: AMT-treated, Staph-Seq cells.

ChIP assays were performed using about 200 million DU145 cells to isolate DNA binding sites of EZH2, which is a rare, low abundance transcription factor. The DNA-EZH2 complexes were immunoprecipitated using an antibody against EZH2 and the DNA-EZH2-antibody complexes were isolated using either untreated Staph A cells or AMT-treated Staph-Seq cells (prepared as detailed in Example 1). GPR101 and SHH are known targets of EZH2 in DU145 cells. In contrast, actin and GAPDH are not EZH2 targets. The specificity of the ChIP assay was validated by qPCR using primers specific for the known targets and non-targets. As shown in FIG. 2, both types of cells isolated complexes comprising the known EZH2 targets and lacking the non-targets.

Both preparations were used to prepare libraries, which were then subjected to Solexa sequencing. As shown in TABLE 2, the use of Staph-Seq cells gave a 23% improvement in the amount of useful (i.e., mappable) sequence generated in the ChIP-Seq experiment.

TABLE 2

ChIP-Seq experiment of chromatin isolated with using untreated and AMT-treated cells

|  | Staph A (control) | Staph-Seq (AMT-treated) |
| --- | --- | --- |
| Total Reads | 45,368,364 | 34,942,887 |
| Mapped Reads (HG19) | 29,878,289 (65.9%) | 31,074,058 (88.9%) |
| Unique | 17,171,199 | 22,200,188 |

This example demonstrates that *Staphylococcus* cells comprising AMT-crosslinked DNA retain their immunoprecipitation functionality but are substantially devoid of contaminating *Staphylococcus* DNA that can be detected by strand separation-based techniques.

What is claimed is:

1. A plurality of isolated, heat-killed, chromosomal DNA interstrand-crosslinked, cell wall protein-crosslinked, protein A-positive *Staphylococcus* cells comprising a plurality of cell wall protein crosslinks and a plurality of chromosomal DNA interstrand crosslinks, wherein the protein A-positive *Staphylococcus* cells are heat-killed, each cell wall protein crosslink comprises a covalently-bound aldehyde crosslinker chosen from formaldehyde, paraformaldehyde, or glutaraldehyde, and each chromosomal DNA interstrand crosslink comprises a covalently-bound ultraviolet light-activated crosslinker chosen from psoralen, 8-methoxypsoralen, 4,5',8-trimethylpsoralen, or 4'-aminomethyl-4,5',8-trimethylpsoralen, wherein a plurality of DNA-protein complexes isolated using the plurality of isolated, heat-killed, chromosomal DNA interstrand-crosslinked, cell wall protein-crosslinked, protein A-positive *Staphylococcus* cells comprises *Staphylococcus* DNA that does not interfere with sequence-independent analysis of DNA in the plurality of DNA-protein complexes, and the plurality of DNA-protein complexes has reduced amplifiable *Staphylococcus* DNA as compared to the same DNA-protein complexes isolated using a plurality of heat-killed, cell wall protein-crosslinked, protein A-positive *Staphylococcus* cells that are devoid of chromosomal DNA interstrand crosslinks.

2. The plurality of isolated, heat-killed, chromosomal DNA interstrand-crosslinked, cell wall protein-crosslinked, protein A-positive *Staphylococcus* cells of claim 1, wherein the plurality of chromosomal DNA interstrand crosslinks comprise 4'-aminomethyl-4,5',8-trimethylpsoralen, and the protein A-positive *Staphylococcus* cells are *Staphylococcus aureus* Cowan strain 1 cells.

3. A method for isolating DNA-protein complexes, the method comprising:
 a) contacting a plurality of DNA-protein-antibody complexes with the plurality of isolated, heat-killed, chromosomal DNA interstrand-crosslinked, cell wall protein-crosslinked, protein A-positive *Staphylococcus* cells as recited in claim 1 such that the plurality of isolated, heat-killed, chromosomal DNA interstrand-crosslinked, cell wall protein-crosslinked, protein A-positive *Staphylococcus* cells bind the plurality of DNA-protein-antibody complexes to form a plurality of protein A-positive *Staphylococcus* cell-bound DNA-protein-antibody complexes; and
 b) contacting the plurality of protein A-positive *Staphylococcus* cell-bound DNA-protein-antibody complexes with an elution buffer to elute a plurality of isolated DNA-protein complexes, wherein the plurality of isolated DNA-protein complexes comprises *Staphylococcus* DNA that does not interfere with sequence-independent analysis of DNA in the plurality of isolated DNA-protein complexes, and the plurality of isolated DNA-protein complexes has an amount of amplifiable *Staphylococcus* DNA that is reduced by at least about 10,000 fold as compared to the same DNA-protein complexes isolated using a plurality of heat-killed, cell wall protein-crosslinked, protein A-positive *Staphylococcus* cells that are devoid of chromosomal DNA interstrand crosslinks.

4. The method of claim 3, wherein the DNA in the plurality of isolated DNA-protein complexes isolated at step (b) is analyzed by a process selected from the group consisting of massively parallel DNA sequencing, sequencing-by-synthesis, sequencing-by-ligation, 454 pyrosequencing, paired-end tag sequencing, cluster amplification, bridge amplification, and PCR amplification.

5. The method of claim 3, wherein the plurality of isolated, heat-killed, chromosomal DNA interstrand-crosslinked, cell wall protein-crosslinked, protein A-positive *Staphylococcus* cells are *Staphylococcus aureus* Cowan strain 1 cells, and the plurality of chromosomal DNA interstrand crosslinks comprise 4'-aminomethyl-4,5',8-trimethylpsoralen.

* * * * *